United States Patent
Kantrowitz et al.

[11] Patent Number: 5,242,415
[45] Date of Patent: Sep. 7, 1993

[54] PERCUTANEOUS ACCESS DEVICE

[75] Inventors: Adrian Kantrowitz, Auburn Hills; Paul S. Freed, Bloomfield Hills, both of Mich.

[73] Assignee: L-Vad Technology, Inc., Auburn Hills, Mich.

[21] Appl. No.: 929,948

[22] Filed: Aug. 14, 1992

[51] Int. Cl.$^5$ .................................. A61M 25/02
[52] U.S. Cl. .................................. 604/175
[58] Field of Search ............... 604/93, 174, 175

[56] References Cited

U.S. PATENT DOCUMENTS

| | | | |
|---|---|---|---|
| 3,826,241 | 7/1974 | Bucalo | 128/1 R |
| 3,906,549 | 9/1975 | Bucalo | 3/1.5 |
| 4,004,298 | 1/1977 | Freed | 3/1 |
| 4,321,914 | 3/1982 | Begovac et al. | 128/1 R |
| 4,393,873 | 7/1983 | Nawash et al. | 604/174 X |
| 4,579,120 | 4/1986 | MacGregor | 604/174 X |
| 4,630,597 | 10/1986 | Kantrowitz et al. | 128/1 D |
| 4,634,422 | 1/1987 | Kantrowitz et al. | 604/175 X |
| 4,897,081 | 1/1990 | Poirer et al. | 604/175 |

*Primary Examiner*—Robert P. Swiatek
*Attorney, Agent, or Firm*—Basile and Hanlon

[57] ABSTRACT

A percutaneous access device includes a body having a horizontal disc-like base flange and a frusto conical projection extending centrally upwardly from one side of the base flange. An elongate flexible tube extends loosely through a bore through the projection and base flange and is sealingly bonded to the body adjacent the bottom of the bore. A coating of a silicone-polycarbonate is applied to the outer surface of the projection and is formed with a multiplicity of microscopic pores to facilitate the bonding of dermal cells to the device upon implantation. The body is of a relatively soft, flexible, biocompatible material so that the device absorbs forces tending to displace the implanted device.

3 Claims, 1 Drawing Sheet

PERCUTANEOUS ACCESS DEVICE

BACKGROUND OF THE INVENTION

I. Field of the Invention

The present invention is directed to a percutaneous access device adapted to be implanted within a patient on a long-term basis.

II. Description of the Related Art

Percutaneous access devices (hereinafter PAD) are employed to provide a through-the-skin coupling or connection between an organ or device implanted within the human body and some external device as, for example, to introduce or withdraw fluids from the patient's body or to establish electrical or pneumatic connections to an implanted device, such as a dynamic aortic patch of the type disclosed in U.S. Pat. No. 4,630,597. The PAD must protrude through the skin and, as set forth in more detail in U.S. Pat. No. 4,634,422, a primary concern is that of preventing the development of infection which is prone to occur at the opening in the skin through which the device projects. U.S. Pat. No. 4,634,422 is directed to a PAD and implanting technique which achieves a firm bond between the underlying dermal layer of the skin and the projecting portion of the PAD to prevent down growth of the epidermal layer of the skin to prevent marsupialization of the PAD and to prevent sinus tract formation caused by epidermal cell proliferation. The PAD of U.S. Pat. No. 4,634,422 includes a removable sleeve which, when assembled on the PAD, forms that portion of the external surface of the projection which passes through the dermal layer. In preparation for implantation, this sleeve is removed from the PAD and its external surface is formed, by nuclear bombardment, with a plurality of tiny pores. A coating of dermal cells is then cultured on this porous surface by techniques described in U.S. Pat. No. 4,634,422, this dermal cell coating growing into the pores of the sleeve surface to firmly mechanically bond the coating to the sleeve surface. Upon reassembly of the sleeve on the PAD and implantation of the PAD into the patient, the dermal cells of the patient will bond to those of the dermal cell coating on the sleeve within a relatively short time to form a barrier layer, preventing down growth of the epidermis along the side of the sleeve.

While the PAD and implantation techniques described in U.S. Pat. No. 4,634,422 present several major advantages over prior art devices, the sleeve employed is of a rigid material. In those applications where the PAD was employed as a plug-in connector to external, electrical or pneumatic devices, rigidity of the projecting portion of the PAD was, to some extent, desirable. However, rigidity of the projecting portion of the PAD made it more likely that tearing of the bond between the PAD and dermal layer would occur if the projecting portion of the PAD or external leads connected to it were inadvertently struck or displaced relative to the skin as by an involuntary movement of the patient.

Forming of the projecting portion of the PAD of a relatively soft, resilient material was not thought practical for several reasons. First, suitable biocompatible materials of sufficient softness and resiliency, if constructed as the sleeve of the PAD of U.S. Pat. No. 4,634,422, would be extremely difficult to handle and manipulate after the dermal layer cell had been cultured on the sleeve, particularly in the step of assembling the sleeve upon the PAD. Second, such materials were found to be very poorly adapted to the formation of microscopic pores of the desired diameter, depth and density, at least by economically feasible techniques. Third, construction of the PAD as a one-piece member, to avoid the first problem referred to above, seemed to require the culturing of a dermal layer over a far larger area of the PAD than would be necessary.

The present invention is directed to a PAD especially designed to be constructed from a soft, resilient material upon which microscopic pores for bonding a layer of dermal cells to the external surface of the PAD may be formed over a minimum area no larger than that essentially required. The PAD is also constructed to minimize displacement of the PAD relative to the patient's skin by movement of external leads or conduits connected to or passing through the PAD.

SUMMARY OF THE INVENTION

In accordance with the present invention, a PAD is constructed from a body of a relatively soft, resilient, biocompatible material, such as silicone. The PAD body is formed as a one-piece member having a horizontally disposed, disc-like base flange with an integral projection projecting upwardly from a central location at the top of the base flange. A vertical bore extends downwardly entirely through the projection and base flange, and an elongate flexible tube of an outer diameter less than that of the inner diameter of the bore through the body passes through and projects from both the top and bottom of the bore. The tube is bonded to the body at the bottom of the bore so that the portion of the tube which extends through the projection is spaced from the side walls of the upper portion of the bore.

The projection is provided with a coating of a copolymer of silicone and polycarbonate, this coating being susceptible to the formation of microscopic bores by the nuclear bombardment and etching technique described in U.S. Pat. No. 4,634,422.

The flexible tube provides a through-the-skin passage which may be employed either as a fluid conducting passage to introduce or withdraw fluids from the patient's body or may constitute a passage through which electrical leads, wire guided instruments, etc. may be passed. By extending the tube for some distance from the projecting portion of the implanted PAD, and anchoring the tube end to the patient's body, forces applied during the connection or disconnection of external devices may be isolated from the PAD.

The copolymer coating of the PAD provides a base upon which a coating of dermal cells may be cultured by the techniques described in U.S. Pat. No. 4,634,422, using a culture and transport chamber of the type described in U.S. application Ser. No. 07/116,311 filed Nov. 4, 1987.

Other objects and features of the invention will become apparent by reference to the following specification and to the drawings.

DESCRIPTION OF THE PREFERRED EMBODIMENT

Figure 1:
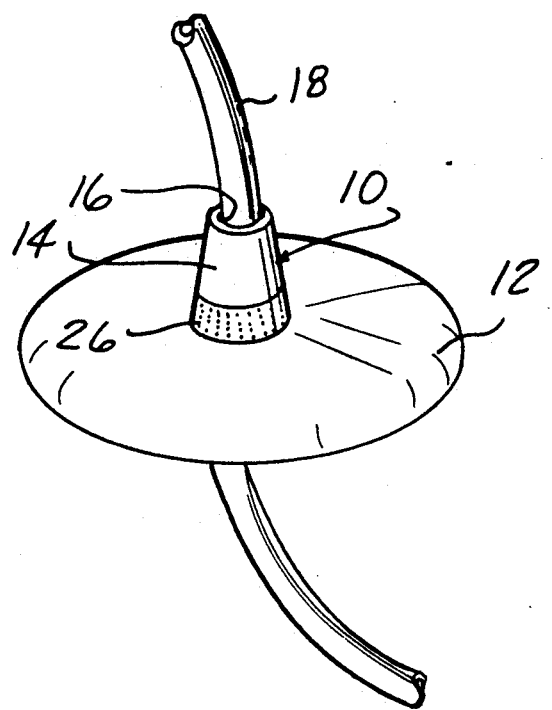
FIG. 1 is a perspective view of a PAD embodying the present invention, with certain parts broken away.
Figure 2:
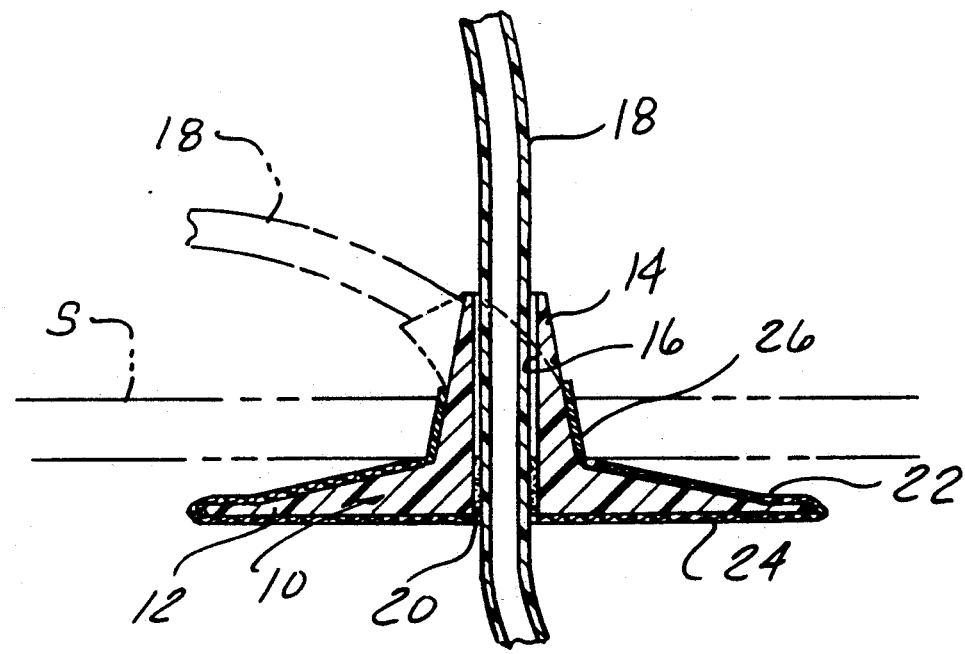
FIG. 2 is a cross-sectional view, taken on a central vertical plane, of the PAD of FIG. 1.

The PAD disclosed in the drawing includes a one-piece molded body designated generally 10 of a relatively soft, flexible and resilient biocompatible silicone material formed with a disc-like base flange 12. An integral, upwardly extending projection 14 is formed at a central location on base flange 12 and projects upwardly from flange 12. A vertical central passage or bore 16 extends downwardly through body 10 from the upper end of projection 14 through the bottom of base flange 12. An elongate flexible tube 18, which may also be of a suitable biocompatible silicone, extends coaxially entirely through central passage 16 and is permanently bonded to body 10 by a suitable bonding material 20 at the lower end of passage 16. As best seen in FIG. 2, the outer diameter of tube 18 is substantially less than the inner diameter of passage 16 so that a clearance exists between the tube and passage throughout substantially the entire portion of the tube within projection 14.

The exterior surfaces of base flange 12 are covered by a layer of Dacron velour material, as at 22, 24. Suitable material for this purpose is commercially available. When the PAD is implanted in a patient, base flange 12 is disposed beneath the skin and the fibrous textured surface of the velour provides a surface into which body tissues may grow and interlock to stabilize the PAD.

A coating of a silicone-polycarbonate copolymer is bonded to the outer side of projection 14. The polycarbonate component of this copolymer provides a surface which can be indented with a multitude of microscopic pores by a nuclear bombardment and etching process as described in U.S. Pat. No. 4,634,422. As described in greater detail in that patent, the microscopic pores provide a surface into which dermal cells can grow to form a multicell layer of dermal cells mechanically bonded to the PAD. Culture and transport devices, such as those disclosed in U.S. patent application Ser. No. 07/116,311, permit the culturing of cells on the microporous surface of band 26.

Referring particularly to FIG. 2, when implanted in the patient, the base flange 12 of the PAD underlies the patient's skin indicated in broken line at S, while the projection 14 of the PAD projects outwardly from the skin. That portion of tube 18 which is implanted in the patient is implanted at the time of implantation of the PAD. The external portion of tube 18, only a portion of which is shown, may be of whatever length is desired. The tube forms a conduit for the passage of fluid, electric leads, guide wires, etc., dependant upon the application. Couplings or electrical connectors may be mounted at the external end of tube 18 at some distance from the PAD itself, thereby effectively isolating the PAD from any disturbance during the connecting or disconnecting of connectors or couplings. As indicated in FIG. 2, the projection 14 is of tapered cross section which narrows toward its open outer end to provide a progressively decreasing resistance to flexing movement as indicated in broken line in FIG. 2 in the event the external portion of the tube might be inadvertently laterally displaced.

While one embodiment of the invention has been described in detail, it will be apparent to those skilled in the art the disclosed embodiment may be modified. Therefore, the foregoing description is to be considered exemplary rather than limiting, and the true scope of the invention is that defined in the following claims.

What is claimed is:

1. A percutaneous access device comprising a body of a relatively soft, flexible, biocompatible material, said body including a generally horizontal base flange and a projection projecting vertically upwardly from the top of said base flange, said body having a bore extending vertically through said projection and base flange, an elongate, flexible hollow tube, having an outer diameter less than the inner diameter of said bore, extending through said bore and projecting outwardly from the opposite ends of said bore, a clearance between said tube and said bore, said clearance extending throughout substantially the entire portion of said tube within said projection, and bonding means sealingly bonding said tube to said body adjacent only the bottom end of said bore, said tube being capable of flexing movement relative to said body within the upper portion of said bore.

2. The invention defined in claim 1 wherein said projection is of a frusto conical configuration and said bore is of a constant diameter whereby the flexibility of said projection progressively increases toward its upper end.

3. The invention defined in claim 1 wherein said material is a silicone, and a coating of a silicone polycarbonate copolymer is bonded to the exterior of said projection adjacent its lower end.

* * * * *